(12) United States Patent
Quinn et al.

(10) Patent No.: US 9,884,052 B2
(45) Date of Patent: Feb. 6, 2018

(54) COMPOUNDS AND METHODS TO TREAT ORGANOPHOSPHORUS POISONING

(71) Applicant: UNIVERSITY OF IOWA RESEARCH FOUNDATION, Iowa City, IA (US)

(72) Inventors: Daniel M. Quinn, Iowa City, IA (US); Joseph John Topczewski, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/951,106

(22) Filed: Nov. 24, 2015

(65) Prior Publication Data
US 2016/0151342 A1 Jun. 2, 2016

Related U.S. Application Data

(62) Division of application No. 14/163,859, filed on Jan. 24, 2014, now Pat. No. 9,249,100.

(60) Provisional application No. 61/756,311, filed on Jan. 24, 2013.

(51) Int. Cl.
| | | |
|---|---|---|
| *A61K 31/44* | (2006.01) | |
| *A61K 31/46* | (2006.01) | |
| *C07D 213/64* | (2006.01) | |
| *A61K 31/5513* | (2006.01) | |
| *A61K 31/4425* | (2006.01) | |
| *A61K 9/00* | (2006.01) | |
| *A61K 45/06* | (2006.01) | |

(52) U.S. Cl.
CPC ........ *A61K 31/4425* (2013.01); *A61K 9/0019* (2013.01); *A61K 31/44* (2013.01); *A61K 31/46* (2013.01); *A61K 31/5513* (2013.01); *A61K 45/06* (2013.01); *C07D 213/64* (2013.01)

(58) Field of Classification Search
CPC .......................... C07D 213/64; A61K 31/4425; A61K 9/0019; A61K 45/06; A61K 31/46; A61K 31/5513; A61K 31/44
USPC ....................................................... 514/221
See application file for complete search history.

(56) References Cited

U.S. PATENT DOCUMENTS

| | | | | |
|---|---|---|---|---|
| 5,180,831 A | * | 1/1993 | Powers | C07D 213/65 540/450 |
| 5,714,615 A | * | 2/1998 | Powers | A61K 31/44 546/291 |

(Continued)

FOREIGN PATENT DOCUMENTS

FR 2605631 * 4/1988

OTHER PUBLICATIONS

Worek; Chemico Biological Interactions, 2011, 194, 91-96.*

(Continued)

*Primary Examiner* — Daniel R Carcanague
(74) *Attorney, Agent, or Firm* — Viksnins Harris Padys Malen LLP (57) ABSTRACT

Organophosphate (OP) nerve agents and pesticides are potent inhibitors of acetylcholinesterase (AChE). Though oxime nucleophiles can reactivate an AChE-phosphyl adduct, the adduct can undergo a reaction called aging, leading to an aged-AChE adduct. The invention provides compounds and methods that can be used to reactivate an aged-AChE adduct. Such compounds and methods are useful to counteract organophosphorus poisoning.

13 Claims, 2 Drawing Sheets

(56) References Cited

U.S. PATENT DOCUMENTS

| | | | | |
|---|---|---|---|---|
| 5,726,314 | A | * | 3/1998 | Powers ............... A61K 31/44 546/291 |
| 9,249,100 | B2 | | 2/2016 | Quinn et al. |
| 2005/0260291 | A1 | * | 11/2005 | Palu .................... A61K 36/746 424/769 |
| 2007/0160700 | A1 | * | 7/2007 | Palu .................... A61K 36/746 424/774 |
| 2009/0023706 | A1 | * | 1/2009 | Albuquerque ......... A61K 31/55 514/215 |

OTHER PUBLICATIONS

Gaso-Sokac; Chemico-Biological Interactions 2010, 187, 234-237.*
Becker; Arch Toxicol 1997, 71, 714-718.*
Becker; Arch Toxicol 2007, 81, 415-420.*
Kondritzer; Journal of Pharmaceutical Sciences, 1961, 50, 109-112.*
Klimmek; Arch Toxicol 1985, 5,7 237-242.*
Cannard; Journal of the Neurological Sciences 2006, 249, 86-94.*
Berge; Journal of Pharmaceutical Sciences 1977, 66, 1-19.*
Paulekuhn; J. Med. Chem. 2007, 50, 6665-6672.*
Brown, "Development of an Effective Therapeutic for Nerve Agent Inhibitied and Aged Acetylcholinesterase", Master's Thesis, Ohio State University, 2012.
Carletti, et al., "Structural evidence that human acetylcholinesterase inhibited by tabun ages through O-dealkylation", J. Med. Chem. 53 (10), 4002-4008 (2010).
Dorwald, "Side Reactions in Organic Synthesis: A Guide to Successful Synthesis Design", Wiley-VCH Verlag GmbH & Co. KGaA, Wienheim, 32 pages (2005).
Ginsburg, "Oximes of the Pyridine Series", Journal of American Chemical Society, 79, 481-485 (1957).
Jokanovic, et al., "Pyridinium oximes as cholinesterase reactivators. Structure-activity relationship and efficacy in the treatment of poisoning with organophosphorus compounds", Curr. Med. Chem. 16, 2177-2188 (2009).
Kalisiak, et al., "Amidine-oximes: reactivators for organophosphate exposure", J. Med. Chem. 54, 3319-3330 (2011).
Kalisiak, et al., "Nonquaternary reactivators for organophosphate-inhibited cholinesterases", J. Med. Chem. 55, 465-474 (2012).
Lodge, et al., "Synthesis and evaluation of human Acetylcholinesterase inhibitors", 47th Midwest Regional Meeting of the American Chemical Society, Omaha, NE, Oct. 24-27, 2012.
Masson, et al., "Structural approach to the aging of phosphylated cholinesterases", Chem. Bio. Interact. 187, 157-162 (2010).
Mercey, et al., "First efficient uncharged reactivators for the dephosphylation of poisoned human acetylcholinesterase", Chem. Commun. 47 (18), 5295-5297 (2011).
Mercey, et al., "Reactivators of acetylcholinesterase inhibited by organophosphorus nerve agents", Acc. Chem. Res. 45 (5), 756-766 (2012).
Millard, et al., "Crystal structures of aged phosphonylated acetylcholinesterase: nerve agent reaction products at the atomic level", Biochem 38 (22), 7032 (1999).
Ohio Supercomputer Center, "Hadad uses supercomputers to test reagents for new treatments", Publication, Apr. 5, 2011.
Quinn, "Acetylcholinesterase: enzyme structure, reaction dynamics, and virtual transition states", Chem. Rev. 87 (5), 955-979 (1987).
Quinn, et al., "Evaluation of Ligands That Alkylate or Acylate the Phosphyl Function of Aged AChE", 7th Annual CounterACT Network Research Symposium, Bethesda, MD, Jun. 25-26, 2013.
Sanson, et al., "Crystallographic snapshots of nonaged and aged conjugates of soman with acetylcholinesterase, and of a ternary complex of the aged conjugate with pralidoxime", J. Med. Chem. 52 (23), 7593-7603 (2009).
Sit, et al., "New structural scaffolds for centrally acting oxime reactivators of phosphylated cholinesterases", J. Bio. Chem. 286, 19422-19430 (2011).
Steinberg, et al., "Model Studies for the Reactivation of Aged Phosphonylated Acetylcholinesterase. Use of Alkylating Agents Containing Nucleophilic Groups", Journal of Medicinal Chemistry, vol. 13 (3), 435-446 (1970).
Topczewski, et al., "Biocompatible Agents Capable of Methylating Phosphonate Anions and the Potential Resurrection of Aged AChE", 6th Annual CounterACT Network Research Symposium, San Francisco, CA, Jun. 26-28, 2012.
Topczewski, et al., "Kinetic Assessment of N-Methyl-2-Methoxypyridinium Species as Phosphonate Anion Methylating Agents", Org Lett 15 (5), 1084-1087 (2013).
Topczewski, et al., "Potential resurrection of aged AChE-OP adducts: design of bio-compatible methyl transfer agents", Presentation at 47th Midwest Regional Meeting of the American Chemical Society, Omaha, NE, Oct. 24-27, 2012.
Topczewski, et al., "Resurrection of an Aged Acetylcholinestrase-Organophosphate Complex", 3rd Postdoctoral Research Symposium, University of Illinois at Urbana Champaign, Champaign, IL, Jan. 25, 2013.
Wandhammer, et al., "A step toward the reactivation of aged cholinesterases—Crystal structure of ligands binding to aged human butyrylcholinesterase", Chemico-Biological Interactions vol. 203 (1), 19-23 (2012).

* cited by examiner

COMPOUNDS AND METHODS TO TREAT ORGANOPHOSPHORUS POISONING

RELATED APPLICATIONS

This patent application is a divisional application of U.S. application Ser. No. 14/163,859, and claims the benefit of priority of U.S. Application Ser. No. 61/756,311 filed Jan. 24, 2013. The content of these applications are hereby incorporated herein in its entirety.

STATEMENT OF GOVERNMENT SUPPORT

This invention was made with government support under Grant No. 5 R21 NS076430 awarded by the National Institutes of Health. The government has certain rights in the invention.

BACKGROUND

Organophosphorus (OP) agents have been used as both pesticides and chemical warfare agents for most of the past century (Mercey, G., et al., *Acc. Chem. Res.* 2012, 45, 756; and Jokanovic, M.; Prostran, M. *Curr. Med. Chem.* 2009, 16, 2177). Pesticides based on phosphate or thiophosphate agents (e.g. parathion, diazinon, or malathion) are or have been used in domestic and commercial agriculture to protect crops from a variety of destructive species. Despite numerous efforts to ban or limit the use of OP pesticides, their continued use results in over 200,000 fatalities and over 1 million instances of morbidity annually due to OP exposure. Phosphonate nerve agents, including sarin, soman, VX, and tabun, are extremely toxic and are considered a serious threat to national security due to their potential use in terrorist actions (See Millard, C. B.; et al., *Biochem.* 1999, 38, 7032; Sanson, B.; et al., *J. Med. Chem.* 2009, 52, 7593; Carletti, E.; et al., *J. Med. Chem.* 2010, 53, 4002; Masson, P.; Nachon, F.; Lockridge, O. *Chem. Bio. Interact.* 2010, 187, 157; and Mercey, G.; et al., *Acc. Chem. Res.* 2012, 45, 756).

Figure 1:
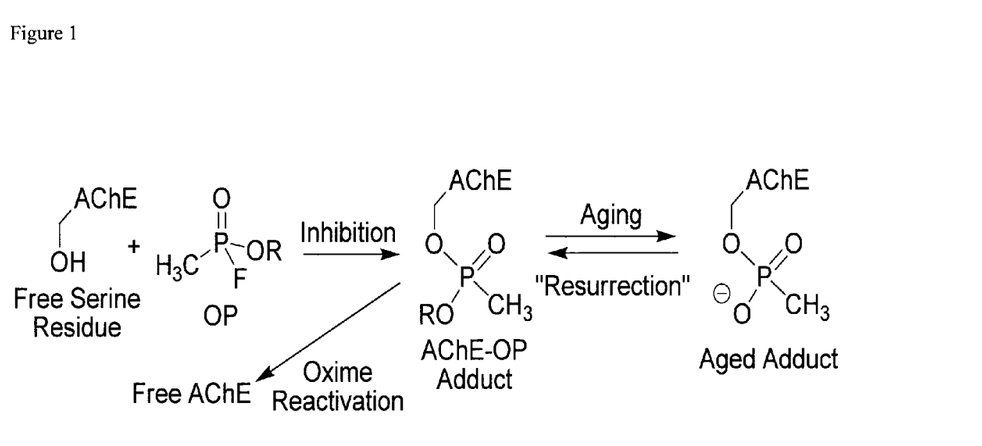
FIG. 1 illustrates an organophosphorous agent (OP) inhibiting acetylcholinesterase (AChE) by covalently bonding to the serine residue in the catalytic triad of the active site to form an AChE-OP Adduct. If administration of an oxime is delayed, a process called aging occurs, wherein the enzyme bound phosphonate experiences a solvolytic loss of an alkyl group (Aging) to form an Aged Adduct. Reactivation (Resurrection) of the Aged-Adduct to provide the AChE-OP Adduct (e.g. using a compound or method of the invention) is also illustrated.

These nerve agents elicit their acute toxicity by inhibiting the acetylcholinesterase (AChE), which results in an overstimulation of muscles due to the buildup of acetylcholine in the neuromuscular junction. The ultimate result is muscle fasciculation and subsequent cardiopulmonary arrest (Mercey, G.; et al., *Acc. Chem. Res.* 2012, 45, 756; and Jokanovic, M.; Prostran, M. *Curr. Med. Chem.* 2009, 16, 2177). Specifically, OPs inhibit AChE by covalently bonding to the serine residue in the catalytic triad of the active site (FIG. 1). The well documented and tremendous affinity of OP agents for the active cite of AChE is a result of OP's structural similarity to the tetrahedral transition state of the cognate hydrolysis reaction of acetylcholine (Quinn, D. M. *Chem. Rev.* 1987, 87, 955).

There are several potential treatments for both acute and chronic organophosphate poisoning. Most include a nucleophilic oxime to reactivate the enzyme along with atropine as an acetylcholine receptor antagonist and diazepam to treat seizures that arise from inhibition of AChE in the CNS (Mercey, G.; et al., *Acc. Chem. Res.* 2012, 45, 756; and Jokanovic, M.; Prostran, M. *Curr. Med. Chem.* 2009, 16, 2177). If administered shortly after exposure, the oxime (e.g. 2-pyridine aldoxime methyl chloride, 2-PAM) is able to displace the bound OP and liberate the serine residue (FIG. 1). (Kalisiak, J.; et al., *J. Med. Chem.* 2011, 54, 3319; Kalisiak, J.; et al., *J. Med. Chem.* 2012, 55, 465; Mercey, G.; et al., *Chem. Commun.* 2011, 47, 5295; and Sit, R. et al., *J. Bio. Chem.* 2011, 286, 19422.)

If administration of the oxime is delayed a process called aging occurs where the enzyme bound phosphonate experiences a solvolytic loss of an alkyl group (FIG. 1: R=isopropyl for sarin, pinacoyl for soman). See Millard, C. B.; et al., *Biochem.* 1999, 38, 7032; Sanson, B.; et al., *J. Med. Chem.* 2009, 52, 7593; Carletti, E.; et al., *J. Med. Chem.* 2010, 53, 4002; Masson, P.; Nachon, F.; Lockridge, O. *Chem. Bio. Interact.* 2010, 187, 157; and Mercey, G.; et al., *Acc. Chem. Res.* 2012, 45, 756. The aged adduct is a phosphonate ester monoanion, which is intrinsically less reactive as an electrophile that the erstwhile neutral phosphonate ester of the initial phosphonyl-AChE adduct. The aged adduct is further stabilized by several key interactions with the AChE active site, and is refractory to oxime reactivation. See Millard, C. B.; et al., *Biochem.* 1999, 38, 7032; Sanson, B.; et al., *J. Med. Chem.* 2009, 52, 7593; Carletti, E.; et al., *J. Med. Chem.* 2010, 53, 4002; and Masson, P.; Nachon, F.; Lockridge, O. *Chem. Bio. Interact.* 2010, 187, 157. No compounds have been reported that are able to recover AChE activity once aging has occurred, and therefore there are no known antidotes against aged AChE-OP adducts. See Mercey, G., et al., *Acc. Chem. Res.* 2012, 45, 756; Kalisiak, J.; et al., *J. Med. Chem.* 2011, 54, 3319; Kalisiak, J.; et al., *J. Med. Chem.* 2012, 55, 465; Mercey, G.; et al., *Chem. Commun.* 2011, 47, 5295; and Sit, R. et al., *J. Bio. Chem.* 2011, 286, 19422.

Currently there is a need for compounds and methods that can be used to reactivate the aged-AChE adduct. Such compounds and methods would be useful to counteract organophosphorus poisoning.

SUMMARY OF THE INVENTION

Applicant has discovered a class of compounds and a method that can be used to reactivate an aged-AChE adduct. Because the aged complex has long been thought of as a dead enzyme, this concept has been termed "resurrection" of the aged adduct (FIG. 1).

Accordingly, the invention provides a method for reactivating an aged-AChE adduct comprising contacting the aged-AChE adduct with an alkylating agent that leads to reactivation of the aged-AChE adduct.

The invention provides a method for treating an animal (e.g. a mammal) suffering from organophosphorus poisoning comprising administering an amount of an alkylating agent effective to reactivate aged-AChE to the animal. The method can further comprise administering an agent capable of reactivating AChE (e.g. a nucleophilic oxime) to the animal. The method can also further comprise administering an acetylcholine receptor antagonist (e.g. atropine) and or an antiseizure agent (e.g. diazepam) to the animal.

The invention provides a method for increasing acetylcholinesterase activity in an animal (e.g. an animal in need of such treatment) comprising administering an amount of an alkylating agent effective to reactivate aged-AChE to the animal. The method can further comprise administering an agent capable of reactivating AChE (e.g. a nucleophilic oxime) to the animal. The method can also further comprise administering an acetylcholine receptor antagonist (e.g. atropine) and or an antiseizure agent (e.g. diazepam) to the animal.

The invention also provides a compound of formula (I):

wherein:
R₁ is (C₁-C₃)alkyl, aryl(C₁-C₃)alkyl, or —Y—Z, wherein any (C₁-C₃)alkyl is optionally substituted with one or more halo, and wherein any aryl is optionally substituted with one or more groups independently selected from halo, cyano, nitro, carboxy, hydroxy, (C₁-C₃)alkyl, (C₁-C₃)alkoxy, (C₁-C₃)alkanoyl, (C₁-C₃)alkoxycarbonyl, (C₂-C₃)alkanoyloxy, and (C₁-C₃)alkylthio, wherein any (C₁-C₃)alkyl, (C₁-C₃)alkoxy, (C₁-C₃)alkanoyl, (C₁-C₃)alkoxycarbonyl, (C₂-C₃)alkanoyloxy, and (C₁-C₃)alkylthio can optionally be substituted with one or more halo;

each R₂ is independently H, halo, cyano, carboxy, —CH=N—OH, (C₁-C₃)alkyl, aryl, heteroaryl, aryl(C₁-C₃)alkyl, or heteroaryl(C₁-C₃)alkyl, wherein any (C₁-C₃)alkyl is optionally substituted with one or more halo, and wherein any aryl or heteroaryl is optionally substituted with one or more groups independently selected from halo, cyano, nitro, hydroxy, (C₁-C₃)alkyl, (C₁-C₃)alkoxy, (C₁-C₃)alkanoyl, (C₁-C₃)alkoxycarbonyl, (C₂-C₃)alkanoyloxy, and (C₁-C₃)alkylthio, wherein any (C₁-C₃)alkyl, (C₁-C₃)alkoxy, (C₁-C₃)alkanoyl, (C₁-C₃)alkoxycarbonyl, (C₂-C₃)alkanoyloxy, and (C₁-C₃)alkylthio can optionally be substituted with one or more halo;

each X is independently a suitable a counter ion;
Y is —(CH₂)ₙ— or —(CH₂)ₙ—O—(CH₂)ₙ—;
n is 1, 2, 3, 4, 5, or 6; and
Z is:

DETAILED DESCRIPTION

The following definitions are used, unless otherwise described: halo is fluoro, chloro, bromo, or iodo. Alkyl denotes both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(Rₓ) wherein Rₓ is absent or is H, O, (C₁-C₄) alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(Rₓ).

The term AChE-OP includes adducts formed when an organophosphorous (OP) agent binds to a residue (e.g. a serine residue) in the catalytic triad of the active site of AChE.

The term aged-AChE adduct includes adducts formed when an AChE-OP adduct experiences a solvolytic loss of an alkyl group.

The term reactivation (or resurrection) describes the process whereby an Aged-Adduct is converted to a corresponding AChE-OP Adduct (e.g. using a compound or method of the invention).

When X is a counter ion it is understood X can be any suitable counterion. Even if it lacks significant AChE resurrecting activity, a salt of formula I can be useful as an intermediate for the preparation or purification of other salts of formula I that have AChE resurrecting activity. Accordingly in the compounds of formula (I), X can be any counterion. For example, in an embodiment of the invention X can be ⁻BF₄, CF₃SO₃⁻, F⁻, Cl⁻, Br⁻, I⁻, monobasic sulfate, dibasic sulfate, monobasic phosphate, dibasic phosphate, or tribasic phosphate, NO₃⁻, P₆⁻, NO₂⁻, carboxylate, CₑF_fSO₃⁻. (where e=2-10 and f=2e+1), or arylsulfonyl, wherein aryl is optionally substituted with one or more groups independently selected from halo, cyano, nitro, carboxy, hydroxy, (C₁-C₃)alkyl, (C₁-C₃)alkoxy, (C₁-C₃)alkanoyl, (C₁-C₃)alkoxycarbonyl, (C₂-C₃)alkanoyloxy, and (C₁-C₃)alkylthio, wherein any (C₁-C₃)alkyl, (C₁-C₃)alkoxy, (C₁-C₃)alkanoyl, (C₁-C₃)alkoxycarbonyl, (C₂-C₃)alkanoyloxy, and (C₁-C₃)alkylthio can optionally be substituted with one or more halo.

An aged-AChE adduct includes enzyme bound phosphonates as described herein that have experienced a solvolytic loss of an alkyl group (for example, see FIG. 1: R=isopropyl for sarin, pinacoyl for soman). The aged adduct can be a phosphonate ester monoanion, which is intrinsically less reactive as an electrophile that the erstwhile neutral phosphonate ester of the initial phosphonyl-AChE adduct.

Specific values listed below for radicals, substituents, and ranges, are for illustration only; they do not exclude other defined values or other values within defined ranges for the radicals and substituents Specifically, (C₁-C₃)alkyl can be methyl, ethyl, propyl, or isopropyl; (C₁-C₃)alkoxy can be methoxy, ethoxy, propoxy, or isopropoxy; (C₁-C₃)alkanoyl can be formyl, acetyl, or propanoyl; (C₁-C₃)alkoxycarbonyl can be methoxycarbonyl, ethoxycarbonyl, propoxycarbonyl, or isopropoxycarbonyl; $(C_1-C_3)$alkylthio can be methylthio, ethylthio, propylthio, or isopropylthio; $(C_2-C_3)$alkanoyloxy can be acetoxy or propanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The compounds of formula I can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should typically be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various other ingredients enumerated above, as required, followed by filter sterilization. In the case of sterile powders for the preparation of sterile injectable solutions, suitable methods of preparation include vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of organophosphorous poisoning.

When the compounds of the invention are administered to counteract organophosphorous poisoning, for example in a chemical warfare situation, they may be self-administered, for example, by means of a syringe or a spring-loaded syringe. When the compounds of the invention are administered as a combination with other agents (e.g. 2-PAM, atropine, and/or diazepam), the combination may also be administered by a single injection device such as, for example, a syringe or a spring-loaded syringe capable of simultaneously administering the one or more of the agents.

Synthesis

The synthesis of the N-methyl-methoxypyridinium compounds can be conducted by exposure of starting pyridines to trialkoxonium (e.g. trimethoxonium) tetrafluoroborate or another alkylating agent (e.g. MeOTf) in a suitable solvent (e.g. methylene chloride or toluene) before or after oxime formation as illustrated in Scheme 1.

The invention will now be illustrated by the following non-limiting Examples.

EXAMPLES

Example 1

Synthesis of the Compound (100)

A 3 mL glass vial was equipped with a rubber septum and magnetic stir bar. The vial was brought into a glove box and charged with trimethyloxonium tetrafluoroborate (198 mg, 1.33 mmol). The vial was sealed and removed from the glove box. A separate 3 mL vial was charged with 2-methoxy-6-pyridinecarboxaldehyde (Aldrich #662933, 184 mg, 1.34 mmol) and was dissolved in $CH_2Cl_2$ (1.5 mL). The solution of pyridine was added via syringe onto the solid trimethoxonium tetrafluoroborate at room temperature. The vial which contained the pyridine was rinsed with $CH_2Cl_2$ (1 mL) and the rinse solution was injected into the reaction vial. The reaction vial was kept at room temperature and stirring was maintained at ca. 400-600 rpm. Over the course of the reaction (17 h), the solid trimethoxonium tetrafluoroborate gradually dissolved, the solution clarified, and an oil gradually formed. At the end of the reaction, hexanes (2 mL) were added after which stirring was stopped. Any solid or oil was allowed to settle and the solvent was removed by glass pipette. The solid or oil was then rinsed with several portions of hexanes followed by diethyl ether. Residual

Scheme 1 solvent was then removed in vacuo to provide the compound N-methyl-6-methoxy-2-pyridinecarboxaldehyde tetrafluoroborate. This oil was used for oxime formation without further purification.

A flask was charged with NaOCH$_3$ (18.5 mg, 0.34 mmol) and hydroxylamine hydrochloride (31 mg, 0.44 mmol) and the solids were taken up in MeOH (2 mL) and left at room temperature for 5 min. The preceding aldehyde (80 mg, 0.34 mmol) was dissolved in MeOH (3 mL) and was injected into the solution of hydroxylamine. After 18 hr at room temperature, the reaction was diluted with ethyl ether, filtered through sand, and concentrated in vacuo. The residue was taken up in acetonitrile and filtered through celite and concentrated in vacuo. The residue was taken up in acetone and slow diffusion of hexanes into the solution provided compound 100 (37 mg, 43%) as a crystalline salt.

Example 2

Synthesis of the Compound (101)

A 3 mL glass vial was equipped with a rubber septum and magnetic stir bar. The vial was brought into a glove box and charged with MeOTf (116 μL, 1.06 mmol) by micropipette. The vial was sealed and removed from the glove box. A separate 3 mL vial was charged with 4-methoxy-2-pyridinecarboxaldehyde (Astatech C10253, 145 mg, 106 mmol) and was dissolved in PhMe (1 mL). The solution of pyridine was added via syringe onto the MeOTf at room temperature. The vial which contained the pyridine was rinsed with PhMe (0.5 mL) and the rinse solution was injected into the reaction vial. The reaction vial was kept at room temperature and stirring was maintained at ca. 400-600 rpm. After 20 h, hexanes (2 mL) were added after which stirring was stopped. Any solid or oil was allowed to settle and the solvent was removed by glass pipette. The solid or oil was then rinsed with several portions of hexanes followed by diethyl ether. Residual solvent was then removed in vacuo to provide the compound N-methyl-4-methoxy-2-pyridinecarboxaldehyde triflate (300 mg, 94%). This oil was used for oxime formation without further purification.

A flask was charged with NaOCH$_3$ (18 mg, 0.34 mmol) and hydroxylamine hydrochloride (27 mg, 0.39 mmol) and the solids were taken up in MeOH (1 mL) and left at room temperature for 5 min. The preceding aldehyde (79 mg, 0.26 mmol) was dissolved in MeOH (2 mL) and was injected into the solution of hydroxylamine. After 18 hr at room temperature, the reaction was diluted with ethyl ether, filtered through sand, and concentrated in vacuo. The residue was purified by C-18 reverse phase chromatography (water/acetonitrile, 0-100%) and concentrated under a stream of air, which afforded compound 101 (18 mg, 22%) as a crystalline salt.

Example 3

Resurrection of Aged-AChE by Compound 100

Recombinant human acetylcholinesterase (hAChE) was irreversibly inhibited by exposure to an organophosphonate (OP) analog of Sarin, 7-(isopropyl methylphosphonyl)-4-methylumbelliferone (Timperley, C. M., et al., *J. Fluor. Chem.*, 2006, 127, 1554-1563). The fully inhibited hAChE-OP adduct was separated on a Sephadex G-50 Quick Spin column to remove excess nerve agent, and it was "aged" for 48 hours at 27° C. Uninhibited hAChE was prepared following the same procedure by substituting acetonitrile in place of the OP inhibitor, and it served as the control throughout the resurrection assay procedure. Hydrolysis of acetylthiocholine (ATCh) by hAChE was measured spectrophotometrically following the Ellman et al. assay method (Ellman, G. L., et al., *Biochem. Pharmacol.*, 1961, 7, 88-95) at t=0 and 48 hours. OP inhibited hAChE was assayed after treatment with 2-pralidoxime (2-PAM) to determine the percentage of "aged" hAChE (% AChE$_{aged}$), or residual hAChE, activity as defined by Equation (1). This % AChE$_{aged}$ is the ratio of the initial rates for OP inhibited hAChE (AChE$_{inhibited}$) and uninhibited hAChE (AChE$_{free}$) catalyzed hydrolysis of ATCh.

$$\% \; AChE_{aged} \; \text{activity} = \frac{\text{rate of } AChE_{inhibited}}{\text{rate of } AChE_{free}} \times 100 \qquad (1)$$

Figure 2:
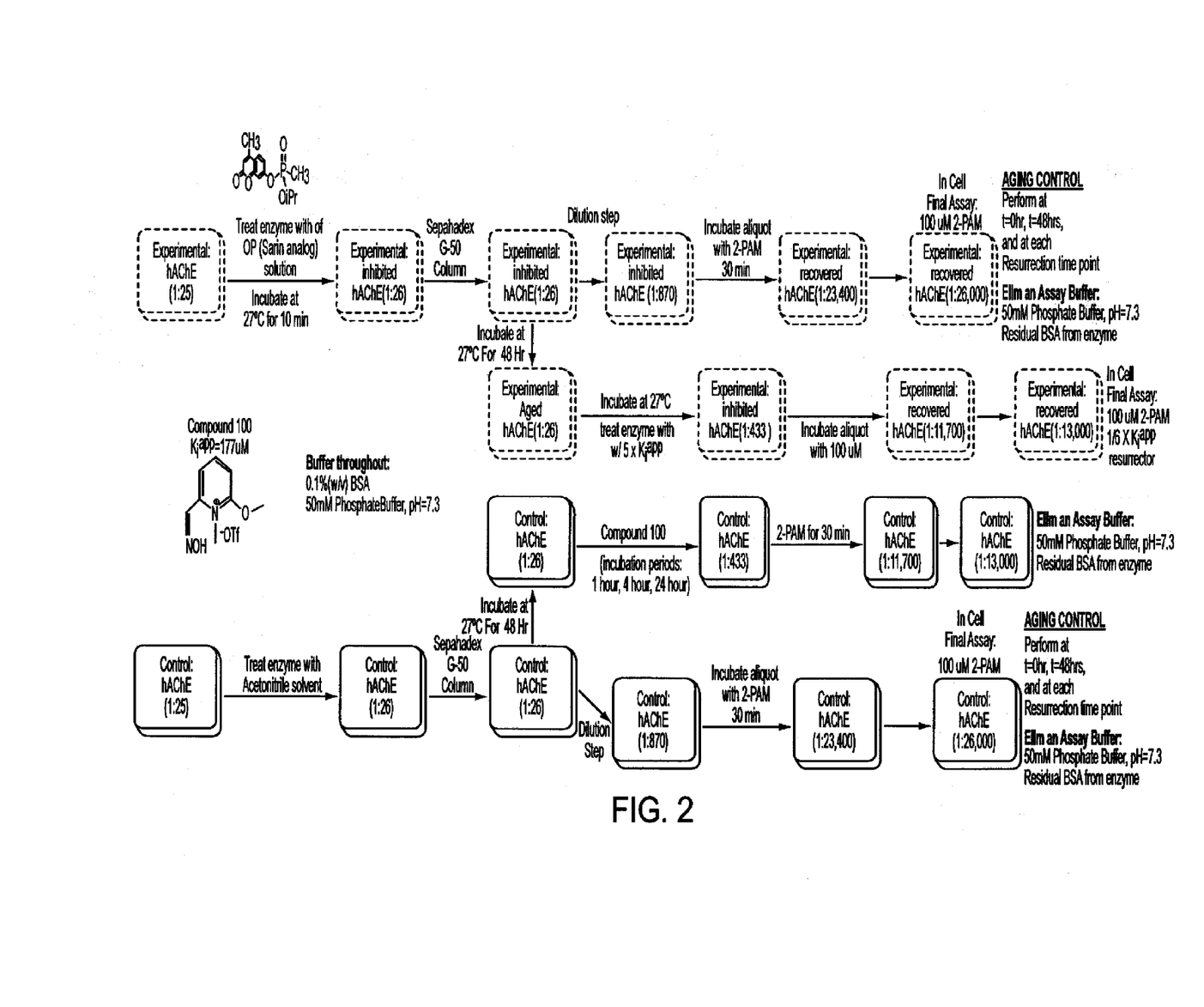
FIG. 2 illustrates the resurrection assay procedure (Example 3) for Compound 100 alkylation and reactivation of "aged" hAChE. The assay was carried out at pH 7.3 and 27° C. Dilution concentrations of hAChE are representative of a 100 μg/mL stock solution of hAChE in 0.1% (w/v) BSA and 50 mM Phosphate Buffer (pH 7.3). The organophosphorus (OP) inhibitor was prepared in acetonitrile.

FIG. 2 depicts the procedural steps for a resurrection assay that can be used to determine the activity of a test compound (e.g. Compound 100). Resurrection assays were performed by preparing a 100 μL incubation solution of 0.024 μg of "aged" hAChE in 0.1% (w/v) BSA, 50 mM phosphate buffer (pH 7.3), and 885 μM Compound 100. "Aged" hAChE was incubated for 1 hour, 4 hour, and 24 hour periods at 27° C. Following each incubation period, a 10 μL aliquot of the "aged" hAChE incubation solution was assayed in 50 mM phosphate buffer (pH 7.3), 0.3 mM ATCh and 0.45 mM DTNB following a 30 minute incubation with 100 μM 2-PAM and a total volume of 300 μL. The percent of "aged" hAChE reactivated (AChE$_{react}$) by 2-PAM was calculated using Equation (2), which is the ratio of the initial rates of "aged" hAChE (AChE$_{aged}$) and AChE$_{free}$ catalyzed hydrolysis of ATCh assayed following each incubation with Compound 100. From Equation (3), the percent of resurrected hAChE was determined.

$$\% \; AChE_{react} \; \text{activity} = \frac{\text{rate of } AChE_{aged}}{\text{rate of } AChE_{free}} \times 100 \qquad (2)$$

$$\% \; AChE_{Res.} \; \text{activity} = \% \; AChE_{React.} \; \text{activity} - \% \; AChE_{aged} \; \text{activity} \qquad (3)$$

Resurrection assay data is shown in the following table for 1.77 mM Compound 100, where $v_i$ is the initial rates for AChE$_{aged}$ and AChE$_{free}$ catalyzed hydrolysis of ATCh. Background rates were measured in the absence of hAChE. All experiments were done in duplicate.

| Time, hours | $v_i$ (AChE$_{aged}$), mA/min | $v_i$ (AChE$_{free}$), mA/min | Background Rate, mA/min | % AChE$_{react}$ | % AChE$_{aged}$ | % AChE$_{Res.}$ |
|---|---|---|---|---|---|---|
| 1.00 | 11.05 (±1.3) | 197.50 (±8.9) | 6.37 (±0.2) | 2.45 (±0.7) | 1.16 (±0.06) | 1.28 (±0.8) |
| 4.00 | 16.66 (±1.0) | 184.70 (±0.7) | 6.56 (±0.1) | 5.67 (±0.6) | 1.16 (±0.06) | 4.50 (±0.6) |
| 12.00 | 20.56 (±0.1) | 191.60 (±28) | 8.75 (±1) | 6.46 (±1.1) | 1.16 (±0.06) | 5.30 (±1.1) |
| 24.00 | 21.90 (±1.5) | 160.70 (±14) | 8.68 (±0.1) | 8.70 (±1.3) | 0.00 (±0.06) | 8.7 (±1.3) |
| 48.00 | 21.75 (±1.3) | 213.60 (±13) | 7.25 (±0.3) | 7.03 (±0.8) | 0.00 (±0.06) | 7.03 (±0.8) |

All publications (including Topczewski et al., *Organic Letters*, 15, 1084-1087 (2013), patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A pharmaceutical composition comprising a compound of the following formula:

wherein:
  $R_1$ is $(C_1-C_3)$alkyl, aryl$(C_1-C_3)$alkyl, or —Y—Z, wherein any $(C_1-C_3)$alkyl is optionally substituted with one or more halo, and wherein any aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
  each $R_2$ is independently H, halo, cyano, carboxy, —CH=N—OH, $(C_1-C_3)$alkyl, aryl, heteroaryl, aryl$(C_1-C_3)$alkyl, or heteroaryl$(C_1-C_3)$alkyl, wherein any $(C_1-C_3)$alkyl is optionally substituted with one or more halo, and wherein any aryl or heteroaryl is optionally substituted with one or more groups independently selected from halo, cyano, nitro, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
  each X is independently $BF_4^-$, $CF_3SO_3^-$, $F^-$, $Cl^-$, $Br^-$, $I^-$, monobasic sulfate, dibasic sulfate, monobasic phosphate, dibasic phosphate, or tribasic phosphate, $NO_3^-$, $PF_6^-$, $NO_2^-$, $CeFfSO_3^-$ (where e=2-10 and f=2e+1), or arylsulfonyl, wherein aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
  Y is —$(CH_2)_n$— or —$(CH_2)_n$—O—$(CH_2)_n$—;
  n is 1, 2, 3, 4, 5, or 6; and
  Z is:

and a pharmaceutically acceptable carrier.

2. A pharmaceutical composition comprising a compound of the following formula:

wherein:
  $R_1$ is $(C_1-C_3)$alkyl, aryl$(C_1-C_3)$alkyl, or —Y—Z, wherein any $(C_1-C_3)$alkyl is optionally substituted with one or more halo, and wherein any aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
  each $R_2$ is independently H, halo, cyano, carboxy, —CH=N—OH, $(C_1-C_3)$alkyl, aryl, heteroaryl, aryl$(C_1-C_3)$alkyl, or heteroaryl$(C_1-C_3)$alkyl, wherein any $(C_1-C_3)$alkyl is optionally substituted with one or more halo, and wherein any aryl or heteroaryl is optionally substituted with one or more groups independently selected from halo, cyano, nitro, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
  each X is independently $BF_4^-$, $CF_3SO_3^-$, $F^-$, $Cl^-$, $Br^-$, $I^-$, monobasic sulfate, dibasic sulfate, monobasic phosphate, dibasic phosphate, or tribasic phosphate, $NO_3^-$, $PF_6^-$, $NO_2^-$, $C_eF_fSO_3^-$ (where e=2-10 and f=2e+1), or arylsulfonyl, wherein aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;

Y is —$(CH_2)_n$— or —$(CH_2)_n$—O—$(CH_2)_n$—;

n is 1, 2, 3, 4, 5, or 6; and

Z is:

and a pharmaceutically acceptable carrier;

further comprising a nucleophilic oxime capable of reactivating an AChE-OP adduct, an acetylcholine receptor antagonist, or an antiseizure agent.

3. The composition of claim 1 that is formulated for administration by injection.

4. A compound of the following formula:

wherein:

$R_1$ is $(C_1-C_3)$alkyl, aryl$(C_1-C_3)$alkyl, or —Y—Z, wherein any $(C_1-C_3)$alkyl is optionally substituted with one or more halo, and wherein any aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;

each $R_2$ is independently H, halo, cyano, carboxy, —CH=N—OH, $(C_1-C_3)$alkyl, aryl, heteroaryl, aryl$(C_1-C_3)$alkyl, or heteroaryl$(C_1-C_3)$alkyl, wherein any $(C_1-C_3)$alkyl is optionally substituted with one or more halo, and wherein any aryl or heteroaryl is optionally substituted with one or more groups independently selected from halo, cyano, nitro, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;

each X is independently $BF_4^-$, $CF_3SO_3^-$, $F^-$, $Cl^-$, $Br^-$, $I^-$, monobasic sulfate, dibasic sulfate, monobasic phosphate, dibasic phosphate, or tribasic phosphate, $NO_3^-$, $PF_6^-$, $NO_2^-$, $C_eF_fSO_3^-$ (where e=2-10 and f=2e+1), or arylsulfonyl, wherein aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;

Y is —$(CH_2)_n$— or —$(CH_2)_n$—O—$(CH_2)_n$—;

n is 1, 2, 3, 4, 5, or 6; and

Z is:

5. A kit comprising 1) the compound of claim 4; and optionally further comprising 2) a nucleophilic oxime capable of reactivating an AChE-OP adduct, 3) an acetylcholine receptor antagonist, and/or 4) an antiseizure agent; and 5) packaging material.

6. The kit of claim 5 wherein one or more of the 1) compound of claim 4; 2) a nucleophilic oxime capable of reactivating an AChE-OP adduct, 3) an acetylcholine receptor antagonist, and 4) an antiseizure agent are packaged in a syringe.

7. The kit of claim 5 wherein the packaging material includes instructions for the administration of the 1) compound of claim 4; 2) a nucleophilic oxime capable of reactivating an AChE-OP adduct, 3) acetylcholine receptor antagonist, and/or 4) antiseizure agent to combat organophosphorous poisoning.

8. The compound of claim 4 which is:

wherein X is $BF_4^-$, $CF_3SO_3^-$, $F^-$, $Cl^-$, $Br^-$, $I^-$, monobasic sulfate, dibasic sulfate, monobasic phosphate, dibasic phosphate, or tribasic phosphate, $NO_3^-$, $PF_6^-$, $NO_2^-$, $C_eF_fSO_3^-$ (where e=2-10 and f=2e+1), or arylsulfonyl, wherein aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo.

9. The compound of claim 8, wherein X is $BF_4^-$.

10. A pharmaceutical composition comprising a compound of formula (I):

wherein:
- $R_1$ is $(C_1-C_3)$alkyl, aryl$(C_1-C_3)$alkyl, or —Y—Z, wherein any $(C_1-C_3)$alkyl is optionally substituted with one or more halo, and wherein any aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
- each $R_2$ is independently H, halo, cyano, carboxy, —CH=N—OH, $(C_1-C_3)$alkyl, aryl, heteroaryl, aryl$(C_1-C_3)$alkyl, or heteroaryl$(C_1-C_3)$alkyl, wherein any $(C_1-C_3)$alkyl is optionally substituted with one or more halo, and wherein any aryl or heteroaryl is optionally substituted with one or more groups independently selected from halo, cyano, nitro, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
- each X is independently $BF_4^-$ or $CF_3SO_3^-$;
- Y is —$(CH_2)_n$— or —$(CH_2)_n$—O—$(CH_2)_n$—;
- n is 1, 2, 3, 4, 5, or 6; and
- Z is:

and a pharmaceutically acceptable carrier.

11. A compound of formula (I):

wherein:
- $R_1$ is $(C_1-C_3)$alkyl, aryl$(C_1-C_3)$alkyl, or —Y—Z, wherein any $(C_1-C_3)$alkyl is optionally substituted with one or more halo, and wherein any aryl is optionally substituted with one or more groups independently selected from halo, cyano, nitro, carboxy, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
- each $R_2$ is independently H, halo, cyano, carboxy, —CH=N—OH, $(C_1-C_3)$alkyl, aryl, heteroaryl, aryl$(C_1-C_3)$alkyl, or heteroaryl$(C_1-C_3)$alkyl, wherein any $(C_1-C_3)$alkyl is optionally substituted with one or more halo, and wherein any aryl or heteroaryl is optionally substituted with one or more groups independently selected from halo, cyano, nitro, hydroxy, $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio, wherein any $(C_1-C_3)$alkyl, $(C_1-C_3)$alkoxy, $(C_1-C_3)$alkanoyl, $(C_1-C_3)$alkoxycarbonyl, $(C_2-C_3)$alkanoyloxy, and $(C_1-C_3)$alkylthio can optionally be substituted with one or more halo;
- each X is independently $BF_4^-$ or $CF_3SO_3^-$;
- Y is —$(CH_2)_n$— or —$(CH_2)_n$—O—$(CH_2)_n$—;
- n is 1, 2, 3, 4, 5, or 6; and
- Z is:

12. The composition of claim 2 wherein the nucleophilic oxime is 2-pyridine aldoxime methyl chloride (2-PAM).

13. The kit of claim 5 wherein the nucleophilic oxime is 2-pyridine aldoxime methyl chloride (2-PAM).

* * * * *

UNITED STATES PATENT AND TRADEMARK OFFICE
CERTIFICATE OF CORRECTION

PATENT NO. : 9,884,052 B2  
APPLICATION NO. : 14/951106  
DATED : February 6, 2018  
INVENTOR(S) : Daniel M. Quinn and Joseph John Topczewski It is certified that error appears in the above-identified patent and that said Letters Patent is hereby corrected as shown below:

In the Claims

Column 11, Line 61, Claim 1, please delete "CeFfSO$_3$-" and insert -- C$_6$F$_5$SO$_3^-$ --;

Column 13, Line 2, Claim 2, please delete "CeFfSO$_3$-" and insert -- C$_6$F$_5$SO$_3^-$ --;

Column 14, Line 4, Claim 4, please delete "CeFfSO$_3$-" and insert -- C$_6$F$_5$SO$_3^-$ --;

Column 15, Lines 45-53, Claim 10, please delete the following structure:

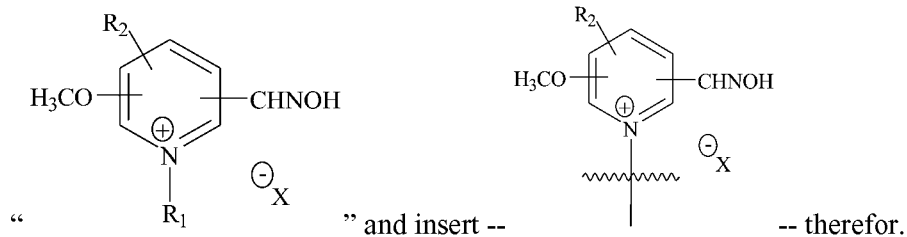

-- therefor.

Signed and Sealed this  
Twenty-sixth Day of June, 2018

Andrei Iancu  
*Director of the United States Patent and Trademark Office*